(12) United States Patent
Brandlhuber et al.

(10) Patent No.: US 8,968,657 B2
(45) Date of Patent: Mar. 3, 2015

(54) TRANSPORT AND HANDLING RETENTION MEMBER

(75) Inventors: Martin Brandlhuber, Wolfgang (DE); Uwe Aulwurm, Velden/Vils (DE)

(73) Assignee: LCTech GmbH (DE)

( * ) Notice: Subject to any disclaimer, the term of this patent is extended or adjusted under 35 U.S.C. 154(b) by 92 days.

(21) Appl. No.: 13/242,779

(22) Filed: Sep. 23, 2011

(65) Prior Publication Data

US 2012/0073703 A1 Mar. 29, 2012

(30) Foreign Application Priority Data

Sep. 28, 2010 (DE) .......................... 10 2010 037 814

(51) Int. Cl.
*G01N 35/04* (2006.01)
*G01N 35/10* (2006.01)
*G01N 35/00* (2006.01)
*B25J 15/08* (2006.01)
*B25J 15/00* (2006.01)

(52) U.S. Cl.
CPC ........... *G01N 35/0099* (2013.01); *B25J 15/086* (2013.01); *G01N 2035/0406* (2013.01); *B25J 15/0028* (2013.01); *G01N 35/1079* (2013.01)
USPC ............ 422/65; 422/63; 422/501; 414/751.1; 436/48; 220/756

(58) Field of Classification Search
CPC .................. G01N 2035/0406; G01N 35/1079; B01L 3/5082; B25J 15/086; B25J 15/0028
See application file for complete search history.

(56) References Cited

U.S. PATENT DOCUMENTS

| 4,705,311 | A | * | 11/1987 | Ragard ............................... 294/2 |
| 4,909,992 | A | * | 3/1990 | Bjorkman ..................... 422/509 |
| 5,242,371 | A | | 9/1993 | Sato et al. |
| 5,360,012 | A | | 11/1994 | Ebara et al. |
| 5,558,200 | A | * | 9/1996 | Whitby et al. ............. 198/470.1 |
| 6,589,789 | B1 | | 7/2003 | Hubert et al. |
| 2002/0102736 | A1 | * | 8/2002 | Kittock et al. ................. 436/48 |
| 2006/0088443 | A1 | * | 4/2006 | Mattila et al. ................... 422/63 |
| 2009/0038709 | A1 | * | 2/2009 | VanVreeland et al. ......... 141/18 |
| 2012/0118903 | A1 | * | 5/2012 | Norton et al. ................. 220/755 |

FOREIGN PATENT DOCUMENTS

| DE | 19840492 A1 | 3/2000 |
| DE | 10210048 C1 | 9/2003 |
| DE | 10302480 A1 | 8/2004 |
| DE | 102004009590 A1 | 9/2005 |
| DE | 202008002435 U1 | 7/2008 |
| DE | 102008028334 A1 | 12/2009 |
| EP | 1361441 A1 | 12/2003 |
| WO | 9514235 A1 | 5/1995 |

* cited by examiner

*Primary Examiner* — P. Kathryn Wright
(74) *Attorney, Agent, or Firm* — Renner Kenner Greive Bobak Taylor Weber

(57) ABSTRACT

The transport and handling retention member comprises an adapter ring which has a central opening for receiving a tubular container for receiving samples, a gripping member for gripping the adapter ring, and a transfer head which can be moved between a rest position and an operating position, the transfer head in the operating position coming into operational contact with a tubular container which is received in the adapter ring.

11 Claims, 6 Drawing Sheets

TRANSPORT AND HANDLING RETENTION MEMBER

TECHNICAL FIELD

The invention relates to a transport and handling retention member for tubular containers for receiving samples, as used in particular in sample preparation systems.

BACKGROUND OF THE INVENTION

An extremely wide variety of systems for preparing samples are known in practice. They mostly have a transport mechanism which can be moved in the x, y and z direction, with the sample receiving member for receiving samples and/or processing devices for processing samples, which are constructed in particular as tubular containers. Tubular containers for receiving/processing samples, such as, for example, cartridges or columns, are arranged in many cases in special processing stations and come into operational contact at that location with a handling device, such as, for example, a needle, in order to supply or remove samples.

There is further known from DE 20 2008 002 435 U1 a transport adapter for tubular containers for receiving samples for laboratory work which is constructed in the form of a combined insertion and fitting head and which comprises an insertable plug portion for closing a tubular container at the upper end and a transport head portion which extends outwards and further has a sealable through-channel for insertion by means of a cannula.

The transport head portion is constructed at the outer side thereof in such a manner that it can be received with a gripping member and moved to a processing station. The plug portion is pressed into the opening of the tubular container. However, this is an article which can be used only once and which further ensures a secure connection in only one processing station in which the tubular container is supported.

SUMMARY OF THE INVENTION

An object of the invention is therefore to set out a transport and handling retention member which ensures secure retention of a tubular container, even during processing outside a processing station.

According to the invention, this object is achieved by the features of claim 1.

The transport and handling retention member according to the invention substantially comprises:

a. an adapter ring which has a central opening for receiving a tubular container for receiving samples,
b. a gripping member for gripping the adapter ring and
c. a transfer head which can be moved between a rest position and an operating position, the transfer head coming into operational contact with a tubular container which is received in the adapter ring in the operating position.

Owing to the combination of the adapter ring with the transfer head, secure retention of the tubular container is possible, which also allows processing outside a processing station. The transport and handling retention member can thereby be universally used.

Whilst the transport adapter described in DE 20 2008 002 435 can be used only in combination with specifically adapted columns, with the transport and handling retention member proposed in this instance it is also possible to use tubular containers of any commercially conventional configuration. Only correspondingly adapted adapter rings are required for different outer diameters of the tubular containers.

The dependent claims relate to other configurations of the invention.

According to a preferred configuration of the invention, the transfer head has a channel which is connected in the operating position to the tubular container received in the adapter ring for the transfer of gas or liquid.

The tubular containers may be constructed so as to be open at the upper ends thereof or closed with a closure mechanism. With open tubular containers, the transfer head is advantageously constructed as a closure element which closes the tubular container received in the adapter ring in a liquid and/or gas-tight manner in the operating position and releases it in the rest position. With a closed tubular container, the transfer head may have a needle or the like for being inserted into the closure mechanism of the tubular container.

However, in both variants of the transfer head the following additional configurations set out below may be provided.

According to a preferred configuration of the invention, the transport and handling retention member is fitted to a transport system which can be moved in the x, y and z direction. Furthermore, the adapter ring may have at the outer peripheral face thereof at least one recess which comes into gripping contact with the gripping member. The gripping movement of the gripping member is carried out, for example, by means of a slotted guiding member. The gripping member and the transfer head may have a common movement mechanism which has a slotted guiding member. It is further advantageous for the gripping member and the transfer head to be retained in a common housing.

The central opening of the adapter ring is further adjoined by a surface region, which serves to support an edge of the tubular container which extends in a flange-like manner. The transfer head itself is formed, for example, by a piston which can be moved in a linear manner, whilst the gripping member has at least two gripping jaws which can each be pivoted about a pivot axis.

The slotted guiding member may have at least one, preferably two slotted members which is/are retained in a central region so as to be able to be pivoted about a pivot axis, the portion which extends from the pivot axis to one end having a slot, a web or a groove and co-operating with a sliding element and the portion which extends from the pivot axis to the other end carrying at least a portion of the gripping member. There may further be provision for the sliding element to be retained on a sliding member, the movement of the sliding member bringing about a displacement of the sliding element in the slotted member and thereby at least partially bringing about pivoting of the slotted member about the pivot axis. The transfer head may further also be secured to the sliding member.

The transfer head may further have a channel which is directed through the transfer head in order to transfer liquid or gas and which, when the transfer head is in the closure position, opens in the region of the central opening of the adapter ring and is thereby connected to a tubular container which is received in the adapter ring for fluid exchange.

BRIEF DESCRIPTION OF THE DRAWINGS

Further advantages and configurations of the invention are explained in greater detail below with reference to the description and the drawings, in which.

DETAILED DESCRIPTION OF ILLUSTRATIVE EMBODIMENTS

Figure 1:
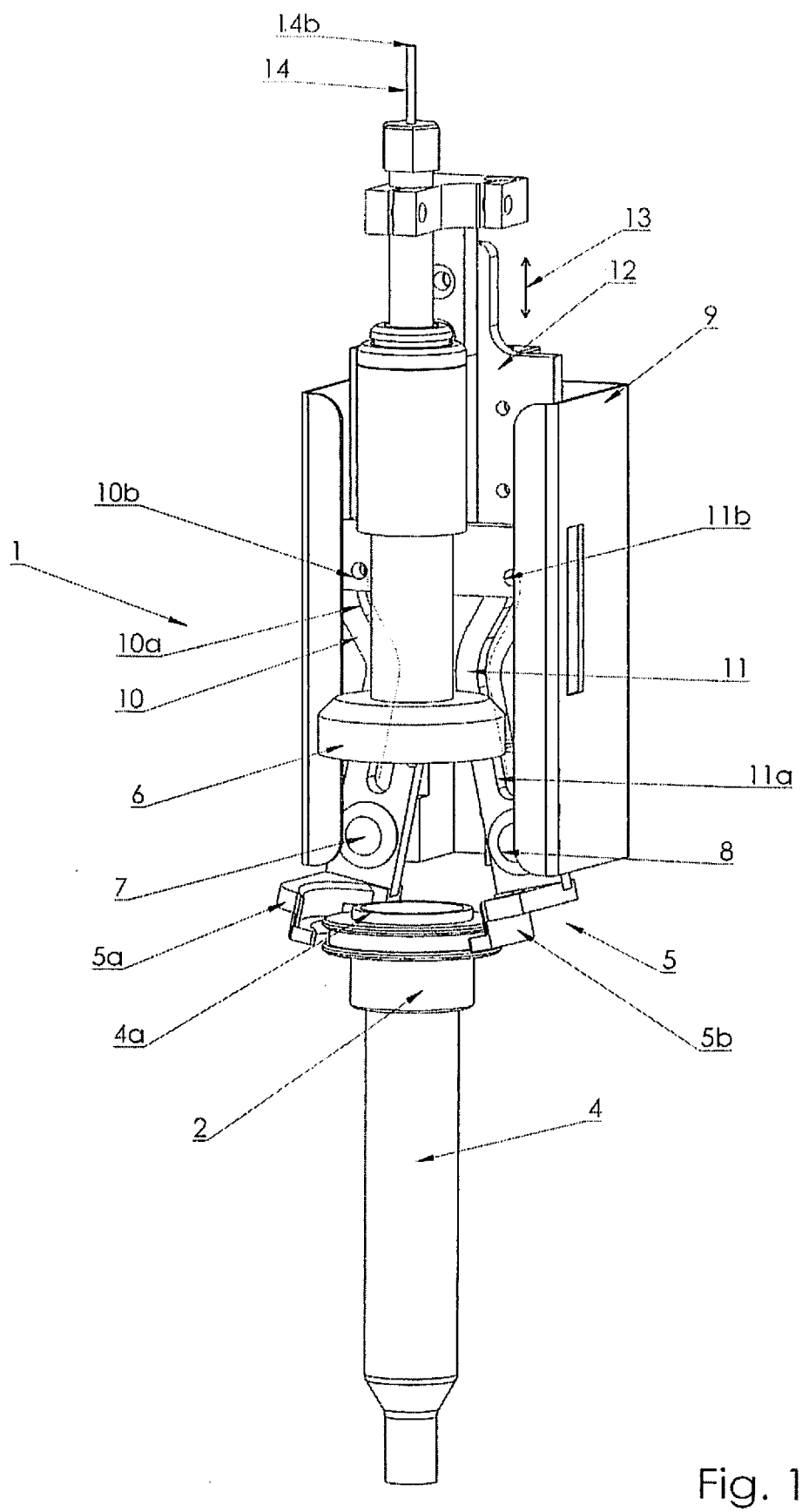
FIG. 1 is a three-dimensional illustration of the transport and handling retention member prior to gripping a tubular container.
Figure 2:
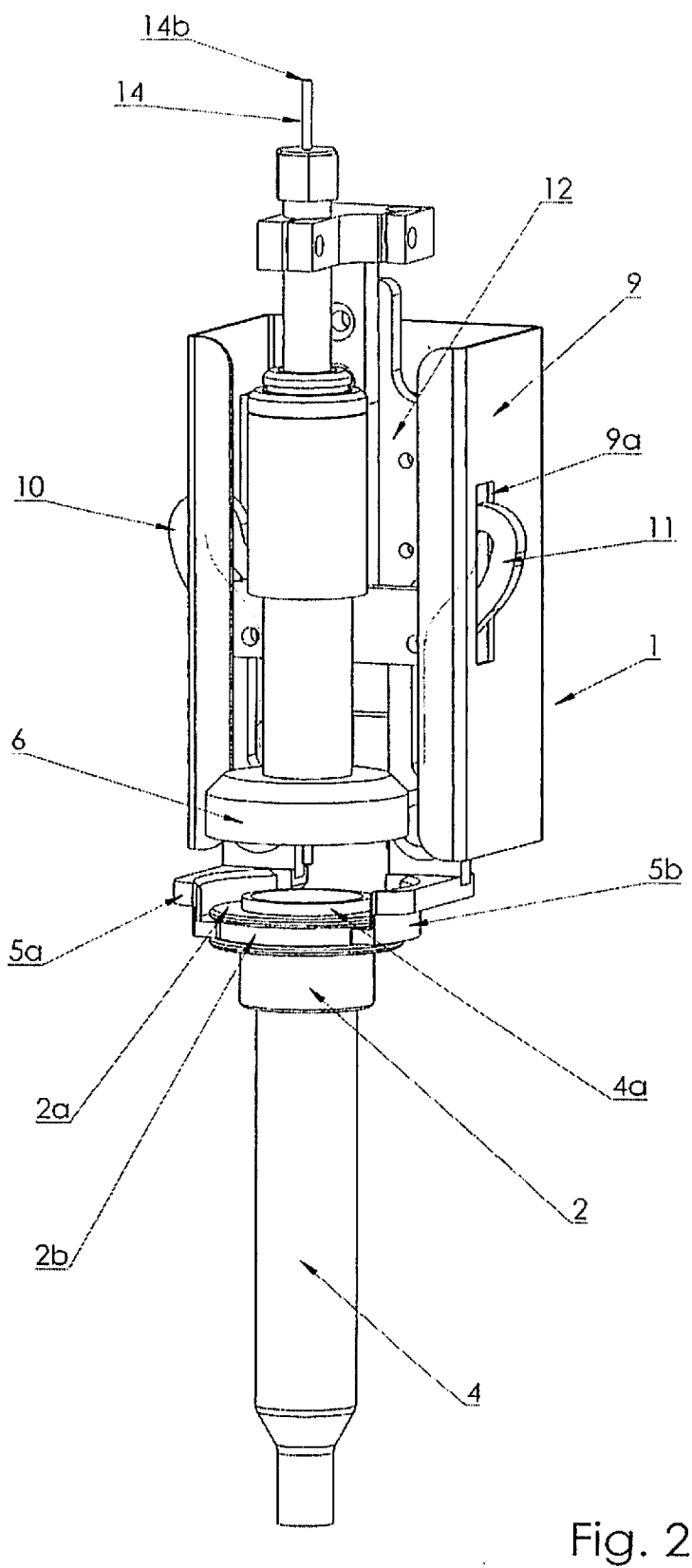
FIG. 2 is a three-dimensional illustration of the transport and handling retention member with the adapter ring gripped and the transfer head in the rest position.
Figure 3:
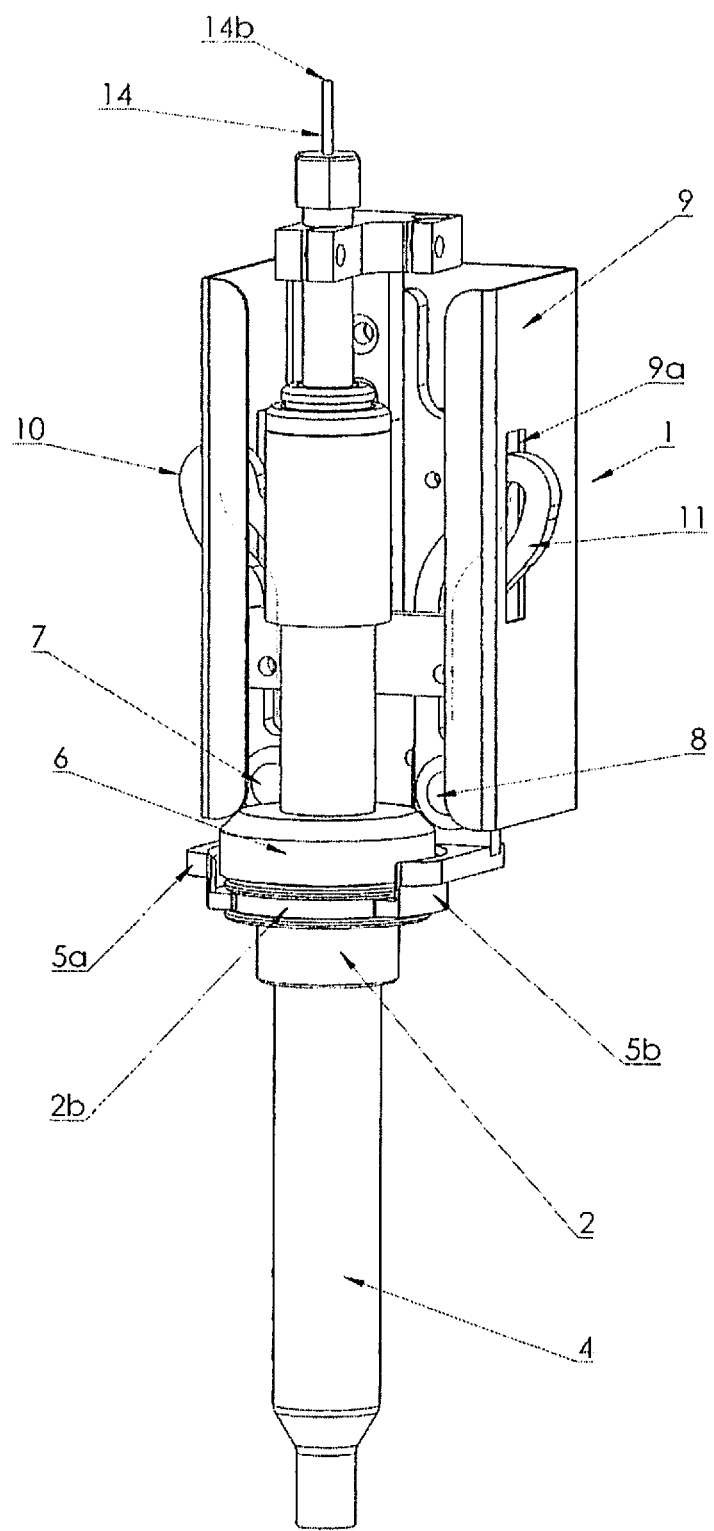
FIG. 3 is a three-dimensional illustration of the transport and handling retention member with the adapter ring gripped and the transfer head in the operating position.
Figures 5, 6:
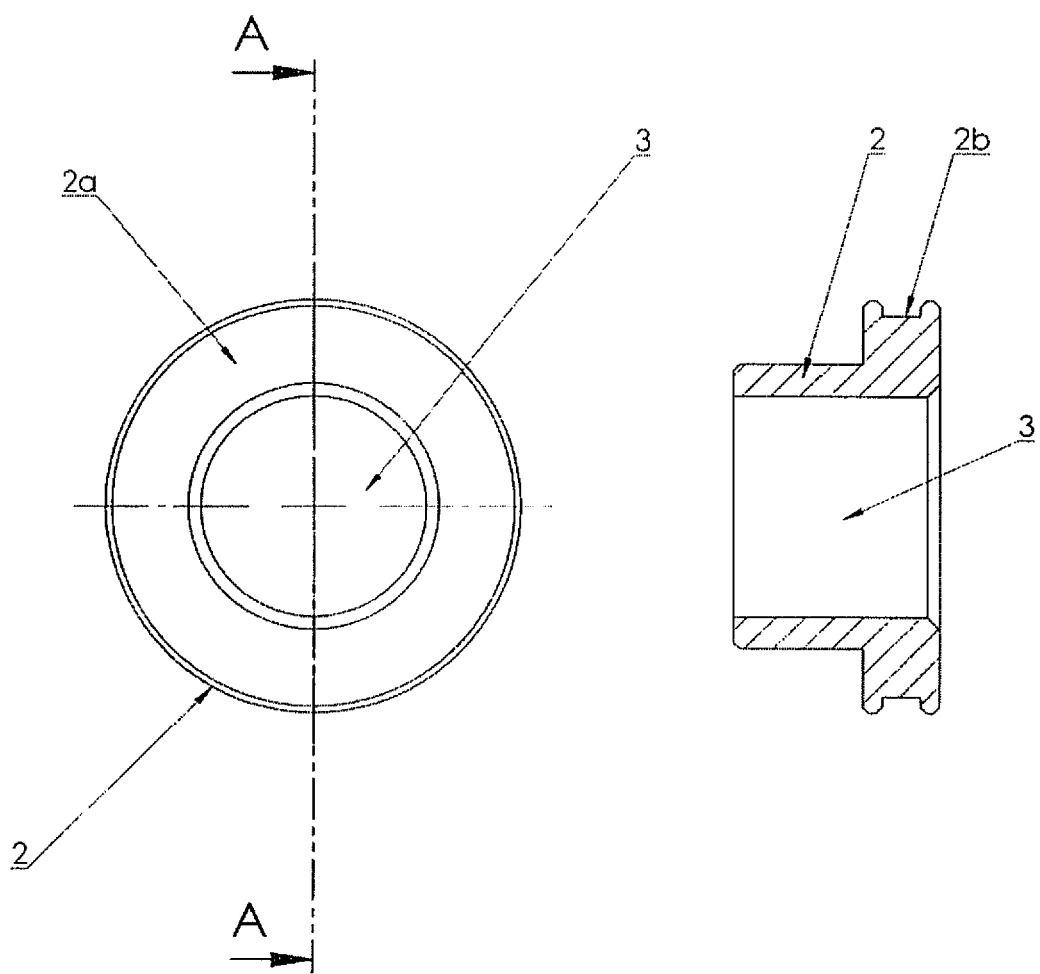
FIG. 5 is a plan view of the adapter ring.
FIG. 6 is a sectioned illustration of the adapter ring along line A-A of FIG. 5

FIGS. 1 to 3 illustrate a transport and handling retention member 1 in various operating positions. It substantially comprises an adapter ring 2 which is illustrated in greater detail in FIGS. 5 and 6 and which has a central opening 3 for receiving a tubular container 4, a gripping member 5 for gripping the adapter ring 2 and a transfer head 6.

The central opening 3 of the adapter ring 2 is adjoined by a surface region 2a which serves to support an edge 4a of the tubular container 4 that extends in a flange-like manner. The adapter ring 2 further has at an outer peripheral face a continuous groove or recess 2b which comes into gripping contact with the gripping member 5. To this end, the gripping member 5 has two gripping jaws 5a, 5b which can each be pivoted about a pivot axis 7, 8.

The transport and handling retention member further comprises a housing 9 in which there is arranged a slotted guiding member with two slotted members 10, 11 which are retained in a central region in the housing 9 so as to be able to be pivoted about the pivot axes 7, 8. The portion which extends upwards from the pivot axis 7 or 8 in each case has a slot 10a, 11a whilst the portion which extends downwards carries both gripping jaws 5a and 5b.

There is further provided in the housing 9 a sliding member 12 which can be moved relative thereto and which carries at the lower end thereof the transfer head 6 which is constructed in the manner of a piston. There are further retained on the sliding member 12 two sliding elements 10b, 11b which engage in the slot 10a and 11a, respectively, in such a manner that a movement of the sliding member 12 brings about a movement of the sliding elements 10b and 11b in the slots 10a and 11a, the slotted members 10, 11 being pivoted about the pivot axes 7, 8 during a first displacement path of the sliding member 12, respectively. The two pivot jaws 5a, 5b of the gripping member thereby pivot together and move into gripping contact with the recess 2b of the adapter ring 2 (see FIG. 2). As soon as the gripping contact is produced, the slots 10a, 11a are aligned parallel with the sliding direction (double-headed arrow 13) so that, with a further movement of the sliding member 12, the transfer head 6 is lowered from its rest position according to FIG. 2 further in the direction towards the tubular container 4 until the transfer head, in the operating position thereof according to FIG. 3, closes the tubular container 4 received in the adapter ring in a liquid- and/or gas-tight manner. To this end, the end face of the transfer head 6 that comes into contact with the edge 4a which extends in the manner of a flange is provided with a suitable sealing element 6a (see FIG. 4).

In the embodiment illustrated, the housing 9 is constructed so as to be relatively narrow so that the slotted members 10, 11 in the phase between the rest position of the transfer head according to FIG. 2 and the operating position of the transfer head according to FIG. 3 protrude from the housing 9 through lateral slots 9a.

The sliding member 12 can be controlled with any suitable actuator.

Figure 4:
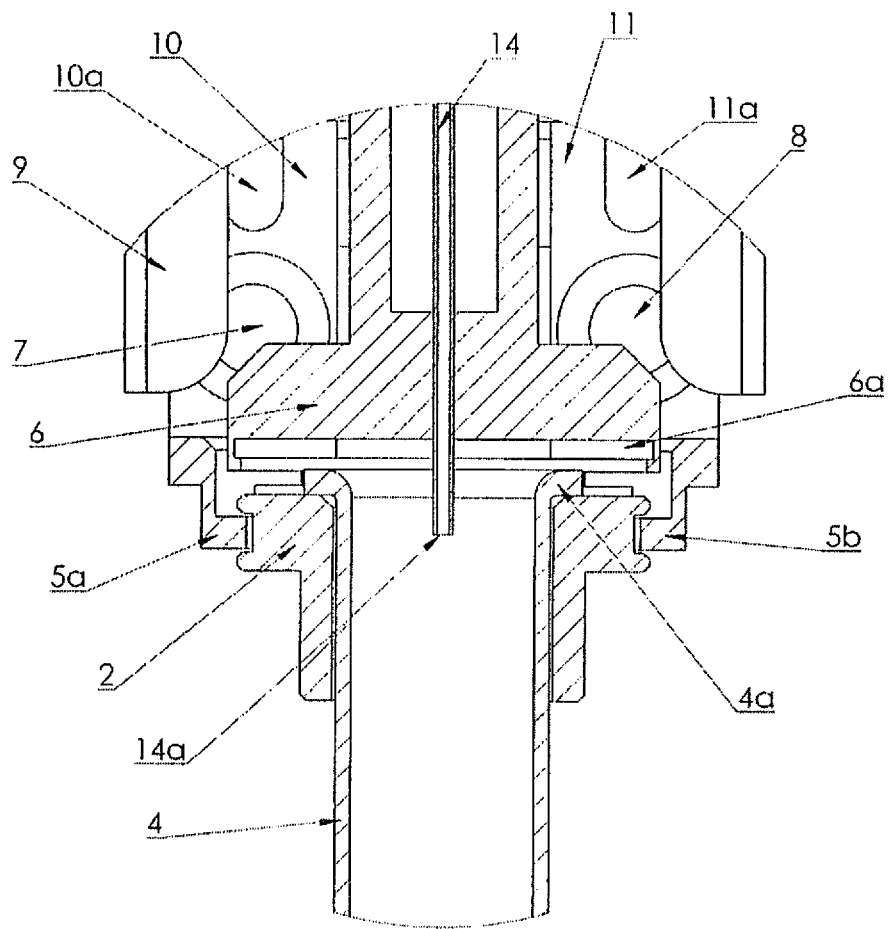
FIG. 4 is a sectioned illustration in the region of the transfer head and adapter ring in the position according to FIG. 3.

FIG. 4 is a sectioned view in the region of the transfer head in the position according to FIG. 3. From this, it can be seen that the tubular container 4 is retained in the region of the flange-like edge 4a thereof on the adapter ring 2a which is in turn fixed by means of the gripping jaws 5a, 5b, whilst the transfer head 6 presses with its sealing element 6a on the edge 4a of the tubular container 4 extending in a flange-like manner, and thereby closes it in a liquid- and/or gas-tight manner.

The transfer head 6 additionally has a central channel 14 which opens at the lower end 14a thereof in the operating position of the transfer head 6 in the upper region of the tubular container 4. The upper end 14b of the channel 14 (see FIGS. 1 to 3) is connected via a pipe which is not illustrated in greater detail to one or more liquid containers or to a sample receiving member. In the operating position according to FIG. 3, the central channel 14 is consequently connected to the tubular container 4 which is received in the adapter ring 2 for fluid exchange.

More detailed configurations in this regard can be taken from the prior application DE 10 2010 037 084, to which reference is hereby made. The transport and handling retention member 1 which is referred to in DE 10 2010 037 084 as a handling device, can consequently be fitted in particular to a transport system which can be moved in the x, y and z direction, the transport and handling retention member 1 being able to be moved in the z direction.

Figure 7:
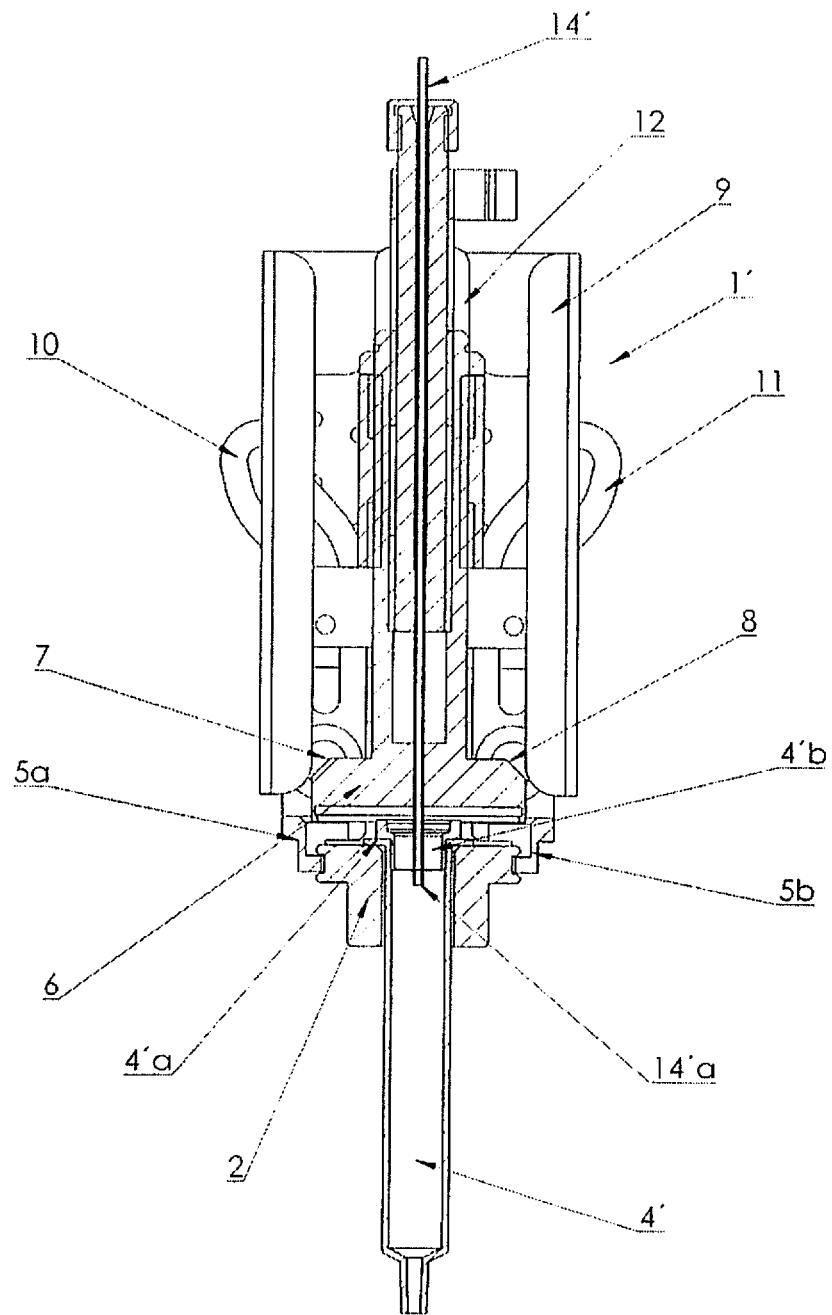
FIG. 7 is a sectioned illustration of a transport and handling retention member in the operating position of the transfer head according to a second embodiment.

FIG. 7 illustrates a second embodiment of a transport and handling retention member 1' which co-operates with a tubular container 4' which is also retained in the adapter ring by means of an edge 4'a which is extended in a flange-like manner but which is also closed by means of a closure mechanism 4'b.

The slotted guiding member with the gripping jaws 5a, 5b and the transfer head 6 are constructed in accordance with the first embodiment and are therefore not explained again in greater detail. The difference is substantially that the central channel 14' is constructed at the lower end 14'a thereof as a needle for being inserted into the closure mechanism 4'b of the tubular container 4' in order to become connected in this manner to the tubular container for fluid exchange.

The two embodiments described above, owing to the secure retention of the tubular container, also allow any samples to be processed outside stationary processing stations. It is thus in particular possible for liquids or gases to be supplied from the rear via the pipe which is connected to the channel. In a configuration according to DE 10 2010 037 084, samples which were received by means of the sample receiver can be directly supplied to the transport and handling retention member 1 for further processing. Since unnecessary movement paths are prevented, extremely efficient and rapid processing of samples is possible.

The retention of the adapter ring with the gripping jaws 5a, 5b allows a very secure and reliable retention which also allows processing of the samples with relatively high compression and tensile forces, such as those which may occur with high flow rates or when removing a needle or stopper.

The invention is claimed:

1. Transport and handling retention member comprising:
an adapter ring having a central opening,
a tubular container for receiving samples, the tubular container received in the adapter ring,
two gripping members for gripping the adapter ring,
a slotted guiding member having two slotted members retained in a central region of a housing so as to be pivotable about a pivot axis, each slotted member includes a portion that extends from the pivot axis to a first end that includes a slot and portion that extends from the pivot axis to a second end that carries a gripping member;
two sliding elements each configured to engage the slot in the slotted guiding member, respectively;
a transfer head movable between a rest position and an operating position;
a sliding member that carries at the lower end thereof the transfer head and the two sliding elements that engage each slot such that movement of the sliding member moves the sliding elements in the slots and the slotted members are pivoted about a pivot axis causing movement of the gripping members and movement of the sliding member causes the transfer head to move between the operational position in contact with the tubular container received in the adapter ring and the rest position not in contact with the tubular container received in the adapter ring.

2. Transport and handling retention member according to claim 1, characterised in that the transfer head is constructed as a closure element that, in the operating position, closes the tubular container received in the adapter ring in a liquid-tight or gas-tight manner, or both, and releases the tubular container in the rest position.

3. Transport and handling retention member according to claim 1, characterised in that the transfer head has a channel that is a needle structured for insertion into a closure mechanism of the tubular container.

4. Transport and handling retention member according to claim 1, characterised in that the transport and handling retention member is fitted to a transport system moveable in the x, y and z direction.

5. Transport and handling retention member according to claim 1, characterised in that the adapter ring has at least one recess at an outer peripheral face thereof that comes into gripping contact with the gripping member.

6. Transport and handling retention member according to claim 1, characterised in that the central opening of the adapter ring is adjoined by a surface region that serves to support a flange that extends from the tubular container.

7. Transport and handling retention member according to claim 1, characterised in that the gripping member and the transfer head are retained in a common housing.

8. Transport and handling retention member according to claim 1, characterised in that the transfer head is constructed in the form of a piston movable in a linear manner.

9. Transport and handling retention member according to claim 1, characterised in that the gripping member has at least two gripping jaws pivotable about a pivot axis.

10. Transport and handling retention member according to claim 1, characterised in that the sliding element is retained on the sliding member, a movement of the sliding member bringing about a displacement of the sliding element in the slotted member and at least partially bringing about pivoting of the slotted member about the pivot axis.

11. Transport and handling retention member according to claim 10, characterised in that the transfer head is secured to the sliding member.

* * * * *